(12) United States Patent  (10) Patent No.: US 7,603,904 B2
Harris et al.  (45) Date of Patent: Oct. 20, 2009

(54) METHOD AND APPARATUS FOR ASSESSING OR PREDICTING THE CHARACTERISTICS OF WOOD

(75) Inventors: Paul David Harris, Lower Hutt (NZ); Alex James Stevenson, Papamoa (NZ); Paul Gamble, Taupo (NZ); Russell John Petherick, Wainuiomata (NZ); Eberhard Juergen Deuss, Pauatahanui (NZ); Eugene Stytsenko, Lower Hutt (NZ); Frederic Lecarpentier, Miramar (NZ); Michael Kenneth Andrews, Pauatahanui (NZ)

(73) Assignee: Waratah NZ Limited, Tokoroa (NZ)

( * ) Notice: Subject to any disclaimer, the term of this patent is extended or adjusted under 35 U.S.C. 154(b) by 299 days.

(21) Appl. No.: 11/352,466

(22) Filed: Feb. 10, 2006

(65) Prior Publication Data

US 2006/0185439 A1   Aug. 24, 2006

Related U.S. Application Data

(60) Provisional application No. 60/652,100, filed on Feb. 11, 2005.

(51) Int. Cl.
*G01N 33/46* (2006.01)
*G01N 29/07* (2006.01)
*G01N 3/30* (2006.01)

(52) U.S. Cl. .............................. 73/597; 73/602; 702/56
(58) Field of Classification Search ........................ None
See application file for complete search history.

(56) References Cited

U.S. PATENT DOCUMENTS 3,066,525 A * 12/1962 Harris ........................... 73/644
3,190,111 A *  6/1965 Trussell et al. ................ 73/600
3,877,294 A *  4/1975 Shaw ............................ 73/584
5,097,881 A    3/1992 Mack
5,307,679 A *  5/1994 Ross ............................. 73/597
5,396,799 A    3/1995 Ross et al.

(Continued)

FOREIGN PATENT DOCUMENTS

CA         2536024         8/2006

(Continued)

OTHER PUBLICATIONS

Andrews, Mike, "Wood quality measurement—son et lumiere", NZ Journal of Forestry, Nov. 2002, pp. 19-21.

(Continued)

*Primary Examiner*—Hezron Williams
*Assistant Examiner*—Rose M Miller
(74) *Attorney, Agent, or Firm*—Darby & Darby P.C.

(57) ABSTRACT

A method and apparatus for determining a characteristic, such as the stiffness, of a portion of a wood specimen characterised by the steps of a) producing an acoustic signal in the wood specimen part way along the length of the wood specimen, and b) sensing a response in the wood specimen part way along the length of the wood specimen including a reverberation from a first end of the wood specimen, and c) calculating a characteristic of a portion of the wood specimen from analysis of the sensed response. A related method and apparatus may be used to determine a characteristic of a portion of a tree stem during harvesting of a tree and the characteristic used to optimise the value of a log cut from the stem.

20 Claims, 7 Drawing Sheets

U.S. PATENT DOCUMENTS

| | | | |
|---|---|---|---|
| 6,026,689 | A | 2/2000 | Snyder et al. |
| 6,276,209 | B1 | 8/2001 | Schafer et al. |
| 6,305,224 | B1 | 10/2001 | Stanish et al. |
| 6,347,551 | B1 | 2/2002 | Turpening et al. |
| 6,598,477 | B2 | 7/2003 | Floyd |
| 6,773,552 | B1 | 8/2004 | Albert et al. |
| 6,813,927 | B1 | 11/2004 | Harris et al. |
| 6,871,545 | B2 | 3/2005 | Huang |
| 6,996,497 | B2 | 2/2006 | Floyd et al. |
| 7,043,990 | B2 | 5/2006 | Wang et al. |
| 7,066,007 | B2 * | 6/2006 | Ziegler et al. ............ 73/12.12 |
| 7,266,461 | B2 | 9/2007 | Huang et al. |
| 7,340,958 | B2 | 3/2008 | Huang et al. |
| 7,383,730 | B2 | 6/2008 | Huang et al. |
| 7,418,866 | B2 | 9/2008 | Wang et al. |
| 2003/0079544 | A1 | 5/2003 | Floyd |
| 2003/0216829 | A1 * | 11/2003 | Andrews et al. ............ 700/167 |
| 2005/0160819 | A1 * | 7/2005 | Wang et al. ................. 73/632 |
| 2005/0216226 | A1 | 9/2005 | Yancey et al. |
| 2006/0000281 | A1 * | 1/2006 | Harris ....................... 73/579 |
| 2006/0185439 | A1 | 8/2006 | Harris et al. |
| 2007/0187022 | A1 | 8/2007 | Biagioni et al. |

FOREIGN PATENT DOCUMENTS

| | | |
|---|---|---|
| CA | 101059221 | 10/2007 |
| GB | 1207375 | 9/1970 |
| JP | 2006241451 | 9/2006 |
| JP | 2007178430 | 7/2007 |
| NZ | 331527 | 3/2000 |
| NZ | 337015 | 7/2000 |
| NZ | 333434 | 7/2001 |
| NZ | 505896 | 12/2002 |
| NZ | 537850 | 10/2006 |
| NZ | 536400 | 5/2007 |
| WO | WO 01/09603 A1 * | 2/2001 |
| WO | WO-0229398 | 4/2002 |
| WO | WO-02/060662 | 8/2002 |
| WO | WO 2006/049514 A1 * | 5/2006 |

OTHER PUBLICATIONS

Carter, Peter, et al. "Acoustic Testing to Enhance Western Forest Values and Meet Customer Wood Quality Needs", Productivity of Western Forests: A Forest Product Focus, 2005, pp. 121-129.

Carter, Peter, et al., "NDE of logs and standing trees using new acoustic tools Technical application and results", 11 pages.

Ross, Robert J., et al., "A Review of the Use of Acoustic Speed to Assess Standing Timber Quality", 5 pages.

Director HM200: Technology for assessment of stiffness in stems and logs, fibre-gen thinking timber, 14 pages.

Assessment of MoE using Acoustic Speed in Wood Director HM200—Student projects, pp. 1-32.

Director ST300—Functionality from Combined Technolgies, 1 page.

Briggs, D., "Non-Destructive Evaluation of Wood Quality in Standing Trees and Logs", 2 pages.

Howe, G.T., et al. "Pacific Northwest Tree Improvement Research Cooperative", 3 pages.

Andrews, M. K. "Proceedings of 123rd International Symposium on Non-Destructive Testing of Wood". Berkeley USA, 2002, pp. 159-165.

Kolsky, H. "Stress Waves in Solids". Oxford at the Clarendon Press, pp. 42-65, 1953.

PNWTIRC: Pacific Northwest Tree Improvement Research Cooperative, Annual Report 2004-2005. Transcription of Text Only.

Director HM200: A Hand Held Tool for Log Segregation, fibre-gen thinking timber. Transcription of Text Only.

Director ST300: A Twin Probe Tool to Assess Wood Quality in Standing Trees, fibre-gen thinking timber. Transcription of Text Only.

Director: Characterizing Wood Quality and Related Values with Acoustic Tools, fibre-gen thinking timber. Transcription of Text Only.

* cited by examiner

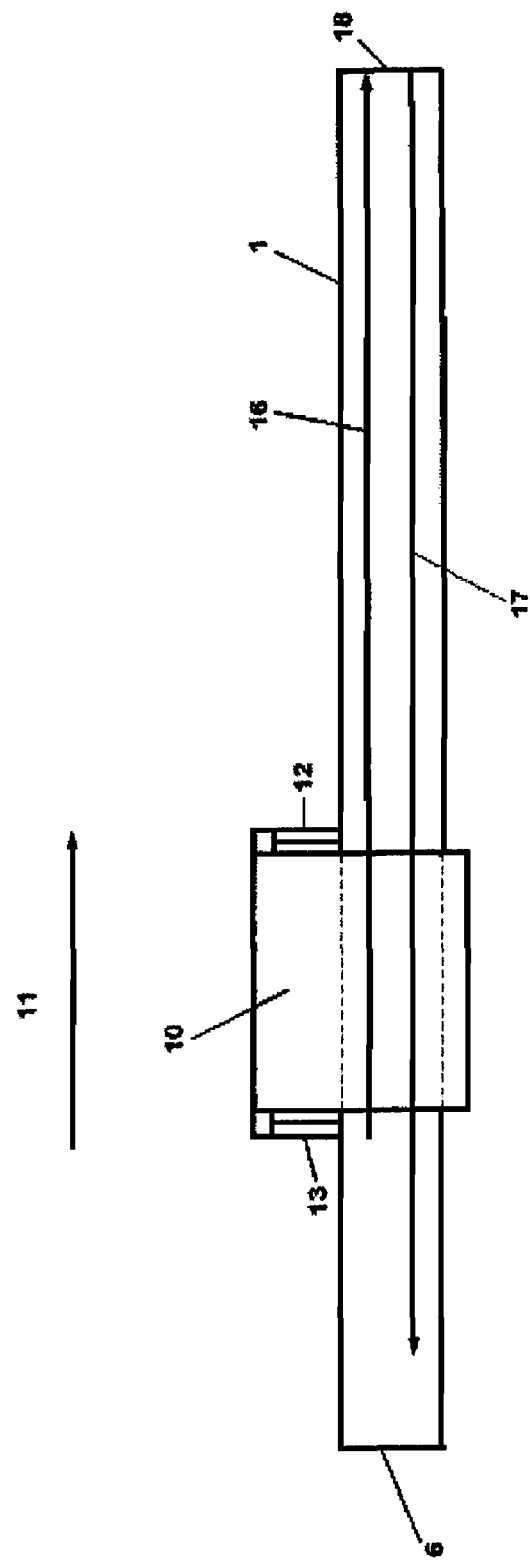

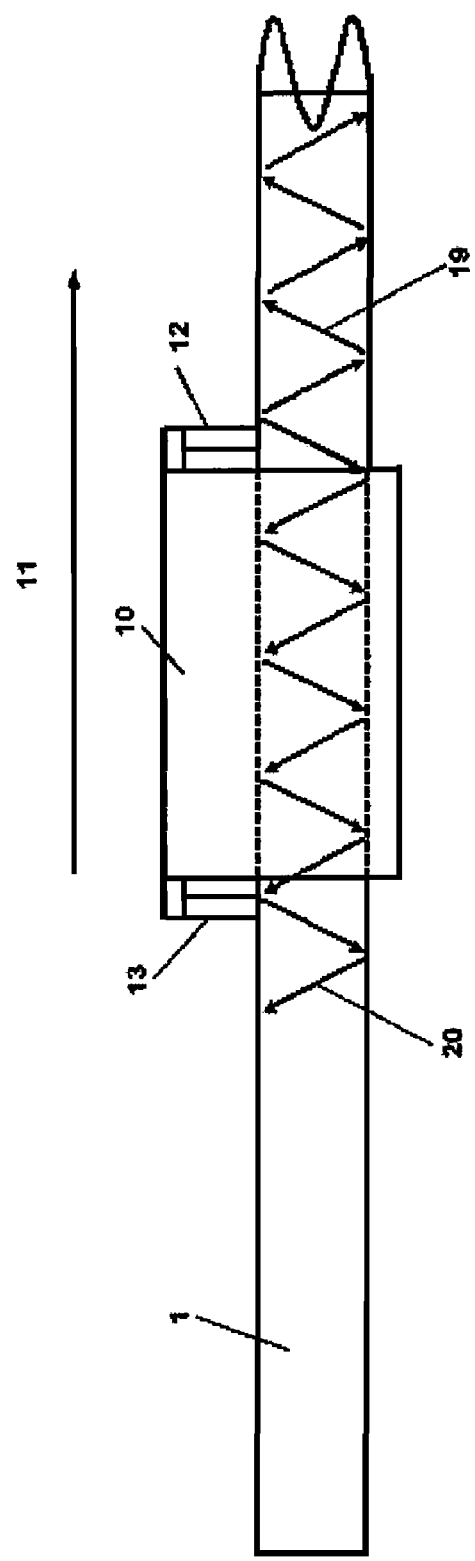

METHOD AND APPARATUS FOR ASSESSING OR PREDICTING THE CHARACTERISTICS OF WOOD

This application claims benefit from U.S. Provisional Patent Application No. 60/652,100 entitled "Method and Apparatus for Assessing or Predicting the Characteristics of Wood," filed on Feb. 11, 2005, the disclosure of which is herein incorporated by reference in its entirety.

FIELD OF INVENTION

The invention relates to a method and apparatus for assessing or predicting the characteristics of wood and in particular to a method and apparatus for acoustically assessing the characteristics of a portion of a stem, log, or other piece of wood.

BACKGROUND

Acoustic technology is increasingly being used in the forestry and processing industries as a means of determining the inherent characteristics of wood and wood composite materials. It is a requirement of the building industry that the strength of a timber piece be sufficient for its purpose.

Utilising longitudinal acoustic signals as a probing means to measure a log's modulus of elasticity provides a convenient measure of stiffness or strength of a wood sample for the forestry industry, as such a measure is largely independent of the cross sectional area of the timber piece. Typically a stress wave is induced in the sample, be it a tree stem, log, or other wood piece, for example, by hitting it with a hammer. The modulus of elasticity can be derived from a measurement of the velocity of the stress wave in the sample length.

One type of instrument measures the time taken for a single traverse of the sample length (transit time) and, knowing the sample length, the acoustic velocity is calculated. This method necessitates transducing both ends of the sample, or alternatively one end of the sample and the hammer.

Most instruments use accelerometers to transduce the disturbance although in some instances displacement transducers are used. Commonly the stress wave is induced directly with a mechanical or pneumatic hammer, however the stress wave may also be induced by an electronic hammer e.g. Silvatest.

Usually the electronic hammer comprises an electronic method of exciting a piezoelectric transmitter or transducer. The controlling electronic signal may be used to indicate the excitation of the sample. The crux is that the stress wave transit time measure is the time measured between excitation of the stress wave and its detection at the receiving transducer.

A limitation to the usefulness of transit timer instruments is that the measure is prone to corruption by noise, due at least in part to the need for wide bandwidths to correctly identify starting and stopping points, and also corruption by other acoustic signals within the sample.

Another type of instrument records the reverberation of the stress wave within the sample for a duration equivalent to many transit periods. A single receiver transducer only is required.

The hit may occur at the same end as the receiving transducer. The hit must contain frequencies which match and excite the resonances of the sample hence ideally an impulse is required which has fast transitions and short period.

The spectral composition of the reverberation is determined typically by Fourier analysis and, knowing the sample length, the velocity calculated.

Since many transits of the sample are recorded the calculated velocity is an average for the recording duration, preferably dominated by the plane wave reverberation.

To accurately determine a sample's velocity it is a requirement that the combination of hit amplitude and material absorption be such that the resonance is recorded for many reverberations. The sample's acoustic absorption dampens the stress wave and imparts an effective window function on the spectral signature. As the absorption increases the resonance peaks broaden resulting in reduced accuracy. Generally resonance is less susceptible to random noise; interference on the other hand appears in the output masquerading as a sample resonance.

In both of the previous instrument types the measured response is of stress waves which have travelled the entire length of the stem. The acoustic velocity calculated from such a response is therefore an average of the entire stem. Those skilled in the art know that the velocity varies along the stem, depending on factors such as, but not limited to, variations in density and stiffness, and the presence of knot whirls and other large discontinuities in the structure.

Therefore a characteristic of the stem determined from the average velocity may differ significantly from the value of the characteristic for a portion of the stem. The average velocity of the stem may be useful in grading whole trees, but cannot be used to determine such things as the location of cuts along the stem in order to maximise the value of the logs. This can only be done using a velocity calculated for the part of the stem about to be cut.

An adaptation on these instrument types, sometimes called a standing tree tool, is to measure a short section of the sample length. Two accelerometers are hit into the log or tree about one metre apart. A stress wave is induced in the log or tree, typically a hit, and a measurement undertaken.

This adaptation suffers from interpretation difficulties relating to the spread of the acoustic signal from the launch point into the bulk of the log or tree and along the surface to the second accelerometer. The pulse may not spread spherically due to the radial velocity profiles within the log or tree, and will not travel as a plane wave.

This adaptation is known to provide a velocity that is also dependant on the diameter of the log. PCT publication WO 02/060662 "System for and method of performing evaluation techniques on a log or round timber" addresses a diameter correction to this adaptation.

Only a small section of a log, in most embodiments about one metre, is measured and it is assumed that this is representative of the tree. However the average values and radial profiles of trees vary notably within the tree, reducing the usefulness of this adaptation.

In forestry applications measurements using the above instruments are either carried out prior to the tree being felled, as in the standing tree tool, or after harvesting when the log has already been cut from the stem.

The instruments described above generally require manual operation. In forestry applications this means provision of safe access to the tree for the operators of the instruments. Access to the stem during the harvesting process, when the information may be of greatest use, is unlikely to be possible or practicable for safety reasons.

Modern harvesting methods increasingly use mechanical harvesters. These machines cut the tree stem from the stump, remove side limbs and in some cases strip bark from the stem prior to cutting the stem into logs of typically around 6 m in length.

It is unsafe to make manual measurements of the stem during this harvesting process, and it is not economical to stop the harvester while the measurement is taken. Therefore the log is generally cut before the physical characteristics (eg stiffness) of the log are determined, thus losing the opportunity to adjust the cut log length to optimize value.

New Zealand Patent No 505896 "Method and Apparatus for assessing or predicting characteristics of wood and other materials" provides an alternative reverberation method. This patent gives an example of a possible harvester head implementation for optimizing log cutting using acoustics to determine an average wood velocity for the complete stem. In this instance the acoustic wave is introduced into the stem by using the harvester head to shake the stem, and reverberation analysis to determine the average velocity of the complete stem.

This method provides information regarding the whole stem rather than the section of the stem about to be cut. It therefore suffers from the same disadvantages as the other "whole of log" methods discussed above. In particular, it cannot be used directly to determine the cutting position and hence to optimize the value of any specific log.

Patents exist considering the detection and grading of logs for defects within a harvester head, for example U.S. Pat. No. 5,097,881 "Ultrasonic log grading". This patent ultrasonically detects internal defects such as knots by analysing the radial response (ie of waves travelling across the stem). The method disclosed does not measure longitudinal sonic velocity as a measure of wood quality and therefore does not provide a measure of (longitudinal) stiffness.

It is an object of the present invention to address the foregoing problems or at least to provide the public with a useful choice.

All references, including any patents or patent applications cited in this specification are hereby incorporated by reference. No admission is made that any reference constitutes prior art. The discussion of the references states what their authors assert, and the applicants reserve the right to challenge the accuracy and pertinency of the cited documents. It will be clearly understood that, although a number of prior art publications are referred to herein, this reference does not constitute an admission that any of these documents form part of the common general knowledge in the art.

It is acknowledged that the term 'comprise' may, under varying jurisdictions, be attributed with either an exclusive or an inclusive meaning. For the purpose of this specification, and unless otherwise noted, the term 'comprise' shall have an inclusive meaning—i.e. that it will be taken to mean an inclusion of not only the listed components it directly references, but also other non-specified components or elements. This rationale will also be used when the term 'comprised' or 'comprising' is used in relation to one or more steps in a method or process.

Further aspects and advantages of the present invention will become apparent from the ensuing description which is given by way of example only.

DISCLOSURE OF INVENTION

According to one aspect the present invention there is provided a method for determining a characteristic of a portion of a wood specimen comprising the steps of
a) producing an acoustic signal in the wood specimen part way along the length of the wood specimen, and
b) sensing a response in the wood specimen part way along the length of the wood specimen including a reverberation from a first end of the wood specimen, and
c) calculating a characteristic of a portion of the wood specimen from the sensed response.

According to another aspect of the present invention there is provided an apparatus for determining a characteristic of a portion of a wood specimen comprising
an acoustic signal generator,
a transmitter configured to provide an acoustic signal from the acoustic signal generator to the wood specimen,
at least one receiver configured to sense acoustic signals within the wood specimen including a reverberation from at least one end, and
a processor electrically connected to the at least one receiver,
characterised in that the processor is configured to determine a characteristic of a portion of the wood specimen from the sensed acoustic signals.

The physical properties of a specimen of a material can be described through knowledge or measurement of standard physical quantities, or characteristics of the specimen. An example of such a characteristic is the modulus of elasticity (MOE) which is a measure of the stiffness of a specimen. The velocity of an acoustic wave in the specimen is another example of a characteristic of a specimen.

The MOE can be defined as the slope of the graph of stress versus strain for a specimen in the region where the response of the material is elastic (ie the stress is proportional to the strain).

The structure and composition of natural materials, such as wood, tend to be variable. In such materials the value of the MOE may vary from specimen to specimen, or for different sections of the same specimen, due to factors such as variations in density or conformation. As wood is very anisotropic the value of the modulus will also depend on orientation.

Knowledge of characteristics, such as the MOE, of the wood specimen can be used to select and grade specimens as appropriate for various uses (for example wood to be used for making furniture, for construction or for pulping). As the value of the wood varies for each of these end uses there is economic advantage in identifying and grading wood specimens at an early stage in the harvesting and processing of timber.

It is well known that the MOE can be measured by determination of the velocity of propagation, v, of an acoustic (stress) wave within the specimen together with the density of the specimen, $\rho$, according to the formula $$MOE = \rho v^2. \tag{1}$$

Throughout this specification the characteristic of the wood sample is taken to be the modulus of elasticity (MOE). However, those skilled in the art would appreciate that other characteristics may also be established from the acoustic properties of the specimen, including the velocity of the acoustic wave in the specimen, and reference to the MOE only throughout this specification should not be considered limiting.

The acoustic signal is applied to the wood specimen at a first position on the wood specimen determined such that the distance from a first end of the wood specimen to the first position on the wood specimen corresponds to a portion of the wood specimen for which the characteristic is to be determined. The portion of the wood specimen for which the characteristic is to be determined will be referred to throughout this specification as the sample portion.

The size of the sample portion will vary depending on the requirements of the situation. For example, in a typical forestry application during harvesting the sample portion of interest is the typical length of a cut log, i.e., around 6 m.

Alternatively for wood to be cut into sections to be used as framing in construction the sample portion is more typically ~3 m.

In a preferred application of the method the acoustic signal is produced by a transducer coupled to the wood specimen. A transducer provides a means of achieving both high energy and a very long lifetime acoustic signal excitation.

The transducer may be a piezoceramic transducer stack. However, those skilled in the art would appreciate that there is a range of devices that may be used to produce an acoustic signal and that reference to a transducer, or to a piezoceramic transducer stack, should not be considered limiting.

The transducer is used to inject a known controlled acoustic signal into the stem. The acoustic signal may be chosen from a wide range of waveforms.

In a preferred application of the method the acoustic signal is in the form of a frequency sweep. For example, the frequency sweep may be in the form of a high power chirp with frequency ranging from 10 kHz to 15 kHz of period 2 ms. Other examples include stepped frequencies, increasing then decreasing frequency sweeps, and non-linear sweeps.

An advantage of using a known controlled acoustic signal is that it allows the use of signal processing techniques, typically filtering and correlation, to extract the signal in a noisy environment, improve the time resolution of a signal, and isolate slower traversing waves from faster longitudinal waves. This provides a considerable advantage in accuracy over simple time-of-flight measurements following an impact.

In a preferred application of the method the transducer is coupled (acoustically) to the wood specimen by use of a spike.

Acoustic coupling should be understood as any means that enables an acoustic signal to be transferred between two or more bodies.

Reference to a spike throughout this specification should be understood to mean any device configured to transmit an acoustic signal from a source exterior to the stem into the interior of the stem.

The spike is used to penetrate the bark layer of the stem (if present) and provide good contact with the stem. The transducer is acoustically coupled to the spike such that the acoustic signal produced by the transducer travels along the spike into the interior of the wood sample. Use of the spike ensures that the acoustic measurement isn't compromised by poor contact with the wood sample.

In alternative applications of the method the acoustic signal is produced by an impact.

Reference to an impact throughout this specification should be understood to mean the action of one body coming forcibly into contact with another. It is well know to those skilled in the art that an impact will create an acoustic signal within the bodies. An impact could be created, for example, by striking the wood specimen with a hammer.

An impact may be provided by directly striking the wood specimen. In other applications the impact may be provided by applying a spike to the wood specimen and striking the free end of the spike.

Throughout this specification reference will be made to an acoustic signal produced by a transducer or by an impact. However, those skilled in the art would appreciate that any well defined acoustic signal may be used and that reference in this specification to a signal produced by a transducer or by an impact, should in no way be considered limiting.

In a preferred application of the method the transducer used to produce the acoustic signal is configured to receive the sensed response. This has the advantage of simplicity in that only one transducer is required to be coupled to the specimen. Furthermore, only one distance measurement is required, being the location of the transmitting transducer relative to an end of the wood specimen.

When the acoustic signal is provided to the wood sample it travels through the wood sample radiating outwardly from the point at which it is provided. The acoustic signal is reflected from the periphery of the wood sample and thus contained within the wood sample.

The transmitted acoustic signal may be resolved into a longitudinal component aligned in the direction of the length of the wood sample, and a radial or transverse component aligned across the wood sample.

The longitudinal component of the signal travels along the wood sample to the end of the wood specimen where it is reflected (at least in part) and travels back along the wood sample. The reflected signal is called a longitudinal reverberation.

Throughout this specification reference to a reverberation should be understood to mean a longitudinal reverberation unless otherwise specified.

A number of reverberations may be created as the signal bounces back and forth between the ends of the wood specimen.

The amplitude of the reverberation may be attenuated through partial scattering of the signal by any large discontinuities, such as knot whirls, if present.

It should be noted that the word stem is used throughout the specification to refer to a wood specimen formed from a felled tree trunk. However, the invention is also applicable to logs, planks, and other embodiments of cut timber. Use of the word stem is by way of example only and should not be construed as limiting the scope of the invention.

For a natural product like wood the acoustic velocity of the reverberation at any point along the stem will vary depending on the type and quality of the wood (eg species, density, conformation, among others) in the vicinity of the point. In the case of recently felled *pinus radiata* stems the acoustic velocity typically increases from about 3 km/s at the butt end of the stem to about 3.5 km/s around 6 m from the butt end, then falls to a value of around 2 km/s at the top of the stem (corresponding to the tree top). The butt end of the stem is the end severed from the stump in felling the tree and represents the oldest wood in the stem.

In a typical forestry situation the stem of a felled tree can be around twenty-five to thirty-five metres long. An acoustic signal produced about six or eight metres from the butt end of the stem has a greater distance to travel to the top of the stem than to the butt end. This greater distance, coupled with the lower velocity in the vicinity of the top end of the stem, means that the reverberation from the butt end of the stem will be received and sensed by the transducer before the reverberation from the top end of the stem.

In a preferred embodiment the method includes the further step of sensing a response at more than one position on the wood specimen. Use of two or more receivers separated along the stem means that the direction of the reverberation can be determined by noting which transducer detects the reverberation, or aspects of it, first.

In other instances, part of the acoustic signal associated with the reverberation may be sensed at one receiver at the same time as an earlier part of the signal is sensed at the other receiver. The time difference between the reverberation signals at each location can be used to determine the direction of travel of the acoustic signal.

In this way a reverberation originating from the first (butt) end of the stem can be distinguished from a reverberation originating from the second (top) end of the stem.

If the reverberation is detected as coming from the stem top, and is unwanted, it can be isolated and at least partially removed from the wanted reverberation signal from the sample portion (normally the butt end).

In alternative embodiments the reverberation originating from the stem top is isolated and used to provide a measure of a characteristic, for example stiffness, of the stem top.

According to the method of the present invention the sensed response includes a single reverberation from at least one end of the wood specimen.

In a preferred embodiment of the present invention the analysis requires only a single reverberation from at least one end of the wood specimen.

In a preferred embodiment of the present invention the method includes the further step of measuring the time delay between the production of the acoustic signal and the sensed response.

In a preferred embodiment the measurement of the time delay between production of the acoustic signal and the sensing of the response for a single reverberation from at least one end of the wood specimen is used to calculate the characteristic of the wood specimen.

The longitudinal acoustic velocity of the sample portion, v, can be established by measuring the time delay, $\Delta t$, between producing the signal at a first position on the stem and sensing at the first position the reverberation from an end, together with the distance, l, of the first position from the end, by using the formula $$v = 2l/\Delta t. \quad (2)$$

This velocity is then used to calculate the MOE for the sample portion using equation (1).

A measure of the density, $\rho$, is also required to calculate the MOE according to equation (1). In practice, for example in order to determine the MOE for a range of specimens from the same wood species, a predetermined average value of the density may be used. However, those skilled in the art will know that not only can the density of wood vary along a specimen, as discussed previously, but may also vary depending on the species and regional factors (soil, climate, etc) which may influence growth of a tree.

Those skilled in the art of forestry will know that the density of trees does vary from tree to tree and from forest to forest. However, in a forest with poor overall density (i.e. overall low value wood) there will still be many trees with an MOE which meets the requirement for higher grade uses, such as structural or veneer/laminate. It is therefore important to test the MOE (for example by measurement of the acoustic velocity) of every tree. The present invention is an improvement on that in that the characteristic of each portion of each tree can be measured.

Those skilled in the art will further appreciate that the measured variations in density, for example of trees of one species within a forest (typically ~10-20%) are insufficient to account for the much greater variations (typically ~200% or more) measured in stiffness (MOE). In this sense the acoustic velocity is a sensitive measure of stiffness. It is therefore anticipated that in practice, for example in a forestry application, the acoustic velocity is likely to be used directly as an indicator of stiffness of a tree, or, as in the present invention, of a portion of a tree stem.

This method of determining the characteristic of the wood sample is very simple, easy to apply and provides an answer very quickly. More importantly it provides a measure of the characteristic of a portion of the sample only, which may be used to grade the portion. This is a major advantage over the prior art methods and instruments which measure a characteristic of the whole sample and therefore cannot be used to grade portions of the sample.

In another application of the present invention the method includes the additional step of using traversing acoustic signals in the wood specimen to determine the characteristic.

Traversing acoustic signals are travelling acoustic waves formed by reflections of the acoustic signal from the outer surface of the wood specimen. Reverberations in the form of traversing acoustic signals contain both longitudinal and radial components.

The radial value of the characteristic of the wood sample determined from the traversing acoustic signals will, for an anisotropic material such as wood, in general be different from the longitudinal characteristic derived from measurement of the longitudinal reverberations as discussed above.

The value of the radial characteristic may assist in determining properties, such as the strength of the radial sections during mechanical deformation, such as occurs during a mechanical pulping process. This information could be used, for example, to determine the suitability of a particular wood specimen for mechanical or chemical pulping.

In a preferred application there is provided a method for determining a characteristic of a portion of a wood specimen during harvesting, characterised by the additional initial step of moving the wood specimen through a harvester head until an end of the wood specimen extends a predetermined length from the harvester head, and wherein the steps b) and c) of the method are carried out proximate to or within the harvester head.

According to another aspect of the invention there is provided a method for determining a characteristic of a portion of a wood specimen during harvesting, characterised by the steps of a) moving a wood specimen through a harvester head until an end of the wood specimen extends a predetermined length from the harvester head, and b) producing an acoustic signal in a portion of the wood specimen proximate to or within the harvester head, and c) sensing a response, including a reverberation from at least one end, in a portion of the wood specimen proximate to or within the harvester head, and d) determining a characteristic of the predetermined length of the wood specimen from the sensed response.

Mechanical harvesters used to fell trees in forestry applications consist of a harvesting head attached to the end of the mechanical arm of a hydraulically operated machine, such as an excavator or wheeled harvester. The harvesting head normally includes a number of wheels used to grip and manoeuvre the stem of the tree, and at least one saw used to sever the stem from the stump. A harvesting head may also include a delimbing knife used to remove side limbs from the stem and other devices for early preparation of the stem.

In normal use the harvesting head is manoeuvred to the base of the tree where the wheels are used to grip the stem. The stem is cut from the stump of the tree using a saw attached to the harvesting head. The wheels are then used to drive the tree stem through the head and any side limbs are removed by de-limbing knives attached to the harvesting head. The stem may also be manoeuvred into position over a stack and cut into lengths using the saw attachment to the harvesting head.

The harvester head is normally instrumented to measure a range of properties of the stem, including its diameter and position relative to the cut (butt) end, as the stem passes through the harvester head. In this way the operator of the harvester may make a cut and move the stem through the harvester head to any predetermined distance from the cut end, as required by the initial step in the method.

In a preferred application of the method the acoustic signal is provided by an acoustic transmitter device attached to the harvester head. Reference throughout this specification to an acoustic transmitter device should be understood to mean any device capable of producing an acoustic signal inside the wood specimen.

In a preferred application the acoustic transmitting device includes a mechanism for producing an acoustic signal.

In a preferred application of the method the mechanism for producing an acoustic signal is a transducer. As discussed above the advantage of using a transducer is that it can be configured to provide a range of controlled and well specified acoustic signals.

An advantage of using a controlled signal, such as that provided by a transducer, in situations such as mechanical harvesting of trees, is that the frequency of the acoustic signal can be chosen to be well separated from the acoustic vibrations introduced into the specimen by the heavy machinery. This simplifies sensing of the response and subsequent signal processing.

In alternative applications of the method the mechanism for producing an acoustic signal is an impact.

In other embodiments the mechanism for producing an acoustic signal may be a shaking device. For example, the harvester head, or some part of it attached to the stem, may be used to shake the stem, thus imparting an acoustic signal into the stem.

In a preferred embodiment the acoustic transmitter device includes a connecting mechanism configured to transmit an acoustic signal from the mechanism for producing the acoustic signal into the wood specimen.

In a preferred embodiment the connecting mechanism is a spike as discussed previously. One end of the spike is driven into the interior of the specimen while the other end is acoustically coupled to the mechanism for producing the acoustic signal.

The advantage of using a connecting mechanism is that the signal, as generated, is produced inside the specimen which in the region for which the characteristic is to be measured. Without the connecting mechanism the signal would be produced by placing the mechanism for producing the acoustic signal against the outer surface of the wood specimen. Typically the outer surface is irregular, especially if covered with bark as is common during harvesting, and does not provide a good acoustic contact. The signal will also be altered by the different properties of the surface layer relative to the properties of the bulk material making subsequent signal processing more difficult.

Attaching the acoustic transmitter device at a fixed position on the harvester head enables the production of the acoustic signal at a known position on the stem within or near the harvester head. As discussed above the orientation and position of the stem (ie the distance of the point on the stem inside the harvester head from the cut end of the stem) are measured at all times as the stem passes through the harvester head. Therefore the location of any fixed point on the harvester head, and particularly the fixed position of the acoustic transmitter device, relative to the cut end of the stem, is known at all times.

The advantage of this arrangement is that the operator of the harvester can move the stem through the harvester head to a known point where the acoustic signal is to be produced, produce the signal and sense the response. The characteristic can then be determined from the sensed response without the requirement for additional distance measurement.

In a preferred embodiment the acoustic transmitter device attached to the harvester head is configured to sense a response to the acoustic signal.

In a preferred application the method includes the further step of sensing a response at a second position in a portion of the wood specimen proximate to or within the harvester head. This is achieved by attaching an acoustic receiver device to the harvester head in a position different from the position of the acoustic transmitter device.

A preferred application of the present invention is to use the characteristic to maximise the value of the cut log. This may be achieved by comparison of the calculated characteristic, or the measured acoustic velocity (as is more likely in practice), with a predetermined table of values characteristic of logs for particular uses. Thus a high value of the acoustic velocity may identify a log suitable for use as a laminate, veneer or high quality lumber; a lower range of values may be indicative of logs for structural uses and saw milling; while values below a lower cut-off value may be indicative of logs to be pulped. For example, for recently felled pinus radiata a value of the acoustic velocity greater than typically ~3.2 km/s is indicative of high value timber; velocity values between ~3.2 km/s and ~2.9 km/s are typically indicative of medium value timber, while values of the velocity below ~2.9 km/s are indicative of wood for low grade structural use or to be pulped.

It is well known, as discussed above, that the velocity varies along the stem. The present invention enables the velocity in a portion of the stem to be determined and used to assess the value of the portion and to determine the position of the cut so as to maximise the value of the cut log.

In a preferred embodiment of the invention there is provided an apparatus for determining a characteristic of a portion of a wood specimen as described above, wherein the transmitter and the at least one receiver are attached to a harvester head.

According to another aspect of the current invention there is provide an apparatus for determining a characteristic of a portion of a wood specimen, the apparatus including an acoustic signal generator, a transmitter configured to provide an acoustic signal from the acoustic signal generator to the wood specimen, at least one receiver configured to detect acoustic signals within the wood specimen including a reverberation from at least one end, and a processor electrically connected to the at least one receiver and arranged to determine a characteristic of the portion of the wood specimen from the detected acoustic signals, wherein the transmitter and the at least one receiver are attached to a harvester head.

The principal advantage of the present invention over the prior art is that it enables determination of a characteristic for a portion of a specimen. The prior art methods generally provide an average value for the characteristic based on measurements of the entire specimen.

In practice the method may be used at a number of positions along a specimen to determine how a characteristic of the specimen varies along its length.

The present method and apparatus have the further advantage that they can be used in situations where the prior art methods and apparatus are not appropriate. In particular this applies in forestry during the harvesting of trees using mechanical harvesters. The prior art methods normally involve manual application. It is not safe, practical or economically worthwhile to apply manual techniques during mechanical harvesting.

The current method can be applied during harvesting by locating the apparatus on the harvester, and in particular by producing and sensing the acoustic signal in or near the harvester head. In this way the method of the present invention can be integrated into the normal operation of the harvester.

After cutting the stem from the stump the operator moves the stem through the harvester head (using the wheels in the harvester head) until reaching a point on the stem within the harvester head where the acoustic signal is to be produced. This is typically the log length (~6 m) but may be any predetermined length.

The acoustic signal is then produced and the response sensed and analysed using a suitably configured computer to produce the required characteristic of the section of the stem between the cut and the harvester head.

Alternatively the signal processor may be configured to measure the response from the end of the stem distal to the cut in order to provide the characteristic of that portion of the stem.

The value of the characteristic is then used, possibly in conjunction with other information, in order to determine the location of the next cut.

There is considerable economic advantage to be gained in using information about a section of the stem, such as its stiffness, in order to determine where to cut the stem so as to optimize the value of the resulting log. The present invention, as described above, provides a method and apparatus to determine the MOE during the harvesting process. Unlike the prior art methods, the present invention can be readily assimilated into the harvesting process.

BRIEF DESCRIPTION OF DRAWINGS

The invention will be further described by way of example only and without intending to be limiting with reference to the following drawings, wherein:

FIG. 6 shows production of an acoustic signal and the path of the acoustic signal to another end of a wood specimen during harvesting; and FIG. 7 shows production of an acoustic signal and the path of the acoustic signal traversing the log cross section in its travel along the wood specimen during harvesting.

BEST MODES FOR CARRYING OUT THE INVENTION

Figure 1:
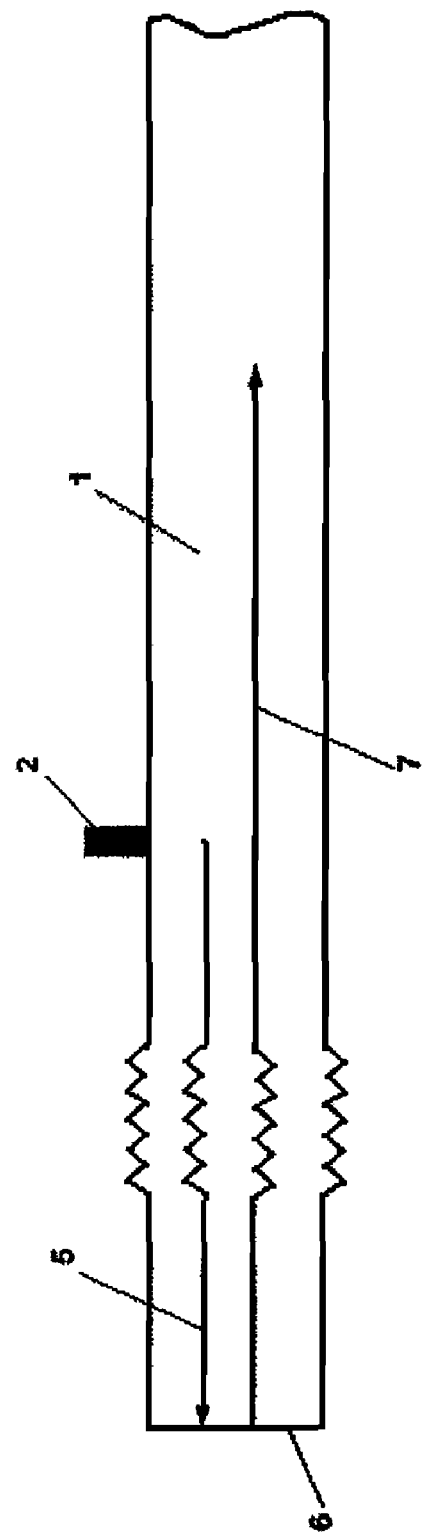
FIG. 1 shows the production of an acoustic signal and the path of an acoustic signal travelling to one end of a wood specimen.

FIG. 1 shows a portion of a wood sample, (1), for which a characteristic, such as the MOE, is to be determined.

An acoustic transmitting device, (2), is used to produce an acoustic signal within the wood specimen, (1).

In a preferred embodiment the acoustic transmitting device, (2), includes a transducer (3) (see FIG. 2) which is connected to a signal generator (not shown).

In other embodiments the acoustic transmitting device, (2), is created by an impact, such as provided by striking the wood specimen, (1), with a hammer (not shown).

Figure 2:
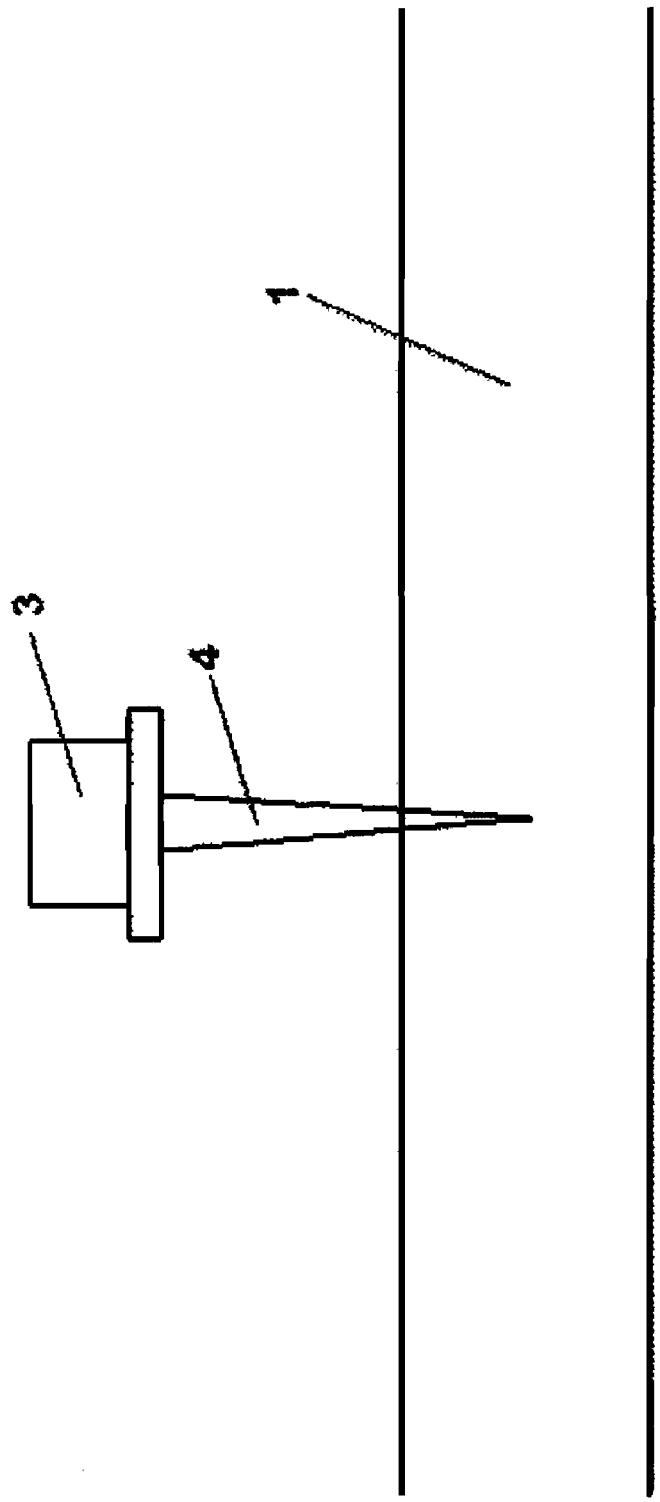
FIG. 2 shows an acoustic transmitting device.

In a preferred embodiment the acoustic transmitting device, (2), includes a connecting mechanism to transfer the acoustic signal provided by the transducer or the hammer, into the interior of the wood specimen, (1). FIG. 2 shows a schematic of an acoustic transmitting device in which a transducer, (3), is acoustically attached to a connecting mechanism in the form of a spike, (4). The spike, (4), in FIG. 2 is shown inserted into the interior of the wood specimen, (1).

The acoustic signal provided by the acoustic transmitter device, (2), creates a stress wave inside the wood specimen, (1), which initially radiates spherically away from the source. Part of the stress wave may be represented as an acoustic signal travelling longitudinally along the length of the wood specimen, (1) in the direction of arrow (5) in FIG. 1. On reaching the end (6) of the wood specimen (1) the acoustic signal is reflected back along the wood specimen (1) in the direction of the arrow (7). This reflected signal is referred to as a reverberation.

In a preferred embodiment the transducer (3) used to produce the initial acoustic signal is configured to sense the reverberations. The transducer (3) is connected to equipment (not shown) for signal processing and analysis which is configured to identify the reverberation.

In practice the reverberation from the end of the specimen (1) closest to the acoustic transmitter device (2) will arrive before reverberations from the other end of the wood specimen (1).

In a preferred embodiment a measurement is made of the time delay, $\Delta t$, between the production of the acoustic signal by the acoustic transmitting device (2) and sensing of the response from a single reverberation from an end (6) of the wood specimen (1).

The velocity, v, of the acoustic signal is determined by $$v = 2l/\Delta t,$$

where l is the distance of the acoustic transmitting device (2) from the end (6) of the wood specimen (1).

The MOE, which is a measure of the stiffness of the wood specimen (1), is then given by $$MOE = \rho v^2.$$

In other applications of the method more complex analysis of the sensed reverberation may be used to establish the acoustic velocity with higher precision.

Figure 3:
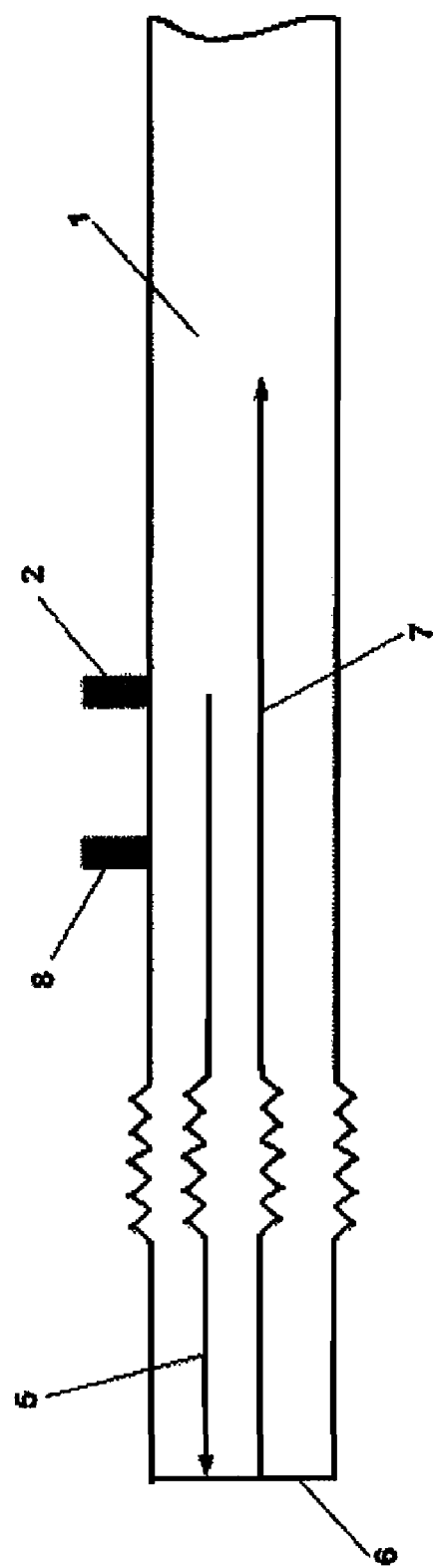
FIG. 3 shows production of an acoustic signal and the path of the acoustic signal to another end of a wood specimen.

FIG. 3 shows a preferred embodiment in which another transducer (8) configured to sense the response, is coupled to the wood specimen (1). The use of two or more transducers placed at different locations along the wood specimen (1) enables the direction of the reverberations to be established by correlation of the signals received at each transducer.

Figure 4:
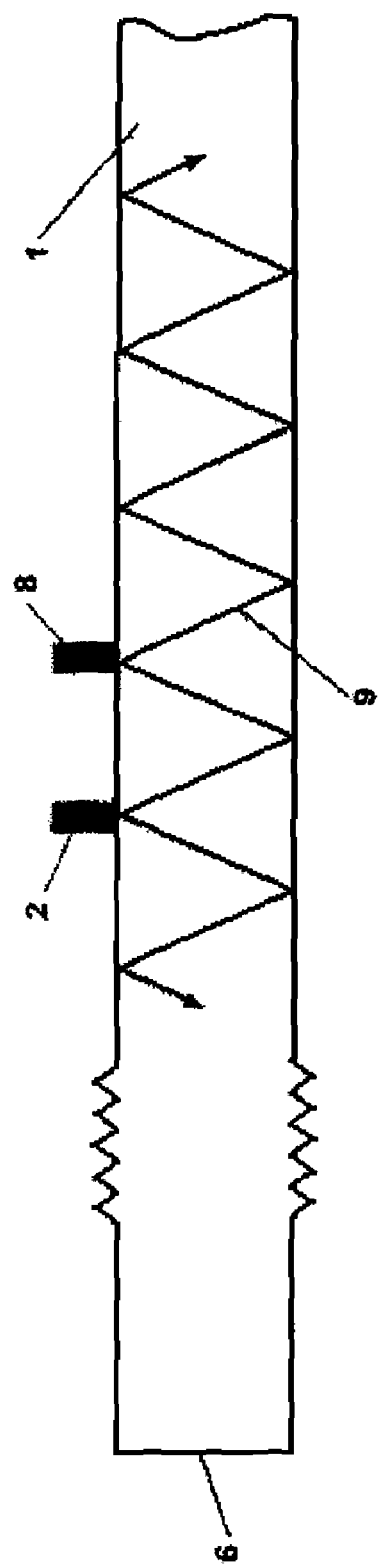
FIG. 4 shows production of an acoustic signal and the path of the acoustic signal traversing the log cross section in its travel along the wood specimen.

FIG. 4 shows a schematic of a transversing acoustic signal (9). As wood is anisotropic the velocity of the transversing acoustic signal will generally be different from the velocity of the longitudinal acoustic signal (depicted in FIG. 1). The velocity of the transversing acoustic signal can be calculated from analysis of the signals received at the transducers (2) and (8). The transversing acoustic signal velocity can be resolved into longitudinal and radial components. The radial acoustic velocity is then calculated from the transversing acoustic signal using the previously calculated value of the longitudinal acoustic velocity (calculated as outlined above).

The invention as outlined above may be applied to any wood specimen. It could, for example, be applied in a saw mill in situations where a characteristic of the wood specimen, such as the stiffness, could be used to determine the length of cut sections (planks) or to grade them. Another situation of particular interest is the application of the method during harvesting of trees.

The description below relates to use of the invention during harvesting of a tree, typically in a forestry application. The wood specimen in this case is the section of the tree cut from the stump, called the stem. This application has the advantage of early identification of characteristics of the portion of interest of the stem, which is then used to optimize the position for cutting the stem.

Figure 5:
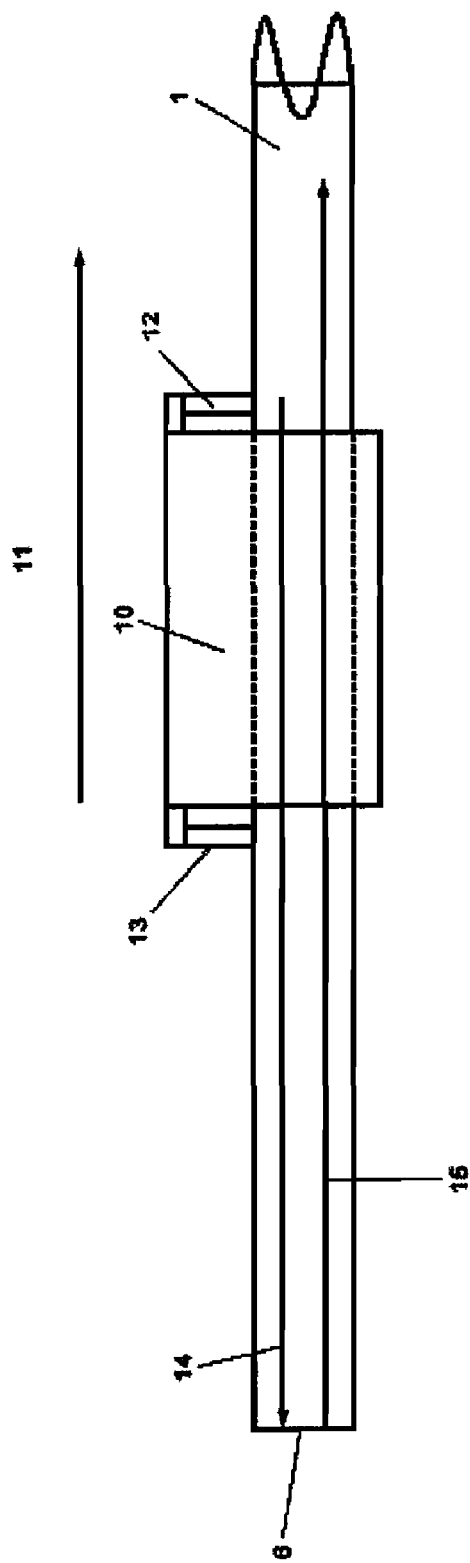
FIG. 5 shows the production of an acoustic signal and the path of an acoustic signal travelling to one end of a wood specimen during harvesting.

In the embodiment of the invention shown in FIGS. 5 to 7 a harvester head (10) is shown around a stem (1). In this embodiment the stem is a recently cut tree.

FIG. 5 shows a portion of a stem (1) during harvesting by a harvester head (10). The harvester head includes delimbing devices (not shown) that strip branches from the stem. The harvester head (10) also includes means (not shown) for moving a stem (1) through the harvester head and an internal chainsaw (not shown) for cutting the stem into lengths. These features of the harvester head are well known.

The harvester head (10) travels along the stem in the direction of the arrow (11). As the harvester head (10) travels along the length of the stem (1) it measures both the length travelled (from the cut end of the stem) and the diameter profile of the stem.

In some embodiments the harvester head (10) may make an initial pass of the stem delimbing the stem and making a rough stem length measurement. During the delimbing pass the harvester head may occasionally slip reducing the accuracy of any length measurement. In these embodiments the acoustic testing and stem cutting is preformed on a second pass. In these embodiments the second pass may begin at the top end of the stem rather than the butt end (6) of the stem.

In preferred embodiments the harvester head (10) also includes at least one acoustic transmitter device (12) capable of imparting an acoustic signal to the stem (1). The acoustic transmitter device (12) is also configured to sense a response in the stem (1).

In one embodiment the acoustic transmitter device (12) includes a spike that penetrates the bark layer of the stem and provides good contact with the stem and a transducer that will provide the acoustic signal (as in the transducer (3) and spike (4) arrangement in FIG. 2).

The acoustic transmitter device (12) includes a spike mount to provide a face for the transducer (3) and a mount to the head frame (not shown). The head frame mount is configured to extend the spike assembly into the stem and to allow the probe assembly to rotate off alignment if the stem rolls while the spike is extended. The spike is retracted following the sensing of the response. Preferably, once the spike is retracted it will self centre.

In alternative embodiments any suitable device may be used to impart an acoustic signal to the stem. For example, an acoustic signal could be created by an impact such as may be provided by applying a spike (4) to the stem (1) and striking the free end of the spike (4).

FIG. 5 shows a direction (14) that an acoustic signal will travel when provided by the acoustic transmitter device (12). The acoustic signal is reflected at the free end (6) of the stem (1) back along the stem in the direction of arrow (15).

In a preferred arrangement the free end (6) is the butt end of the stem. In this instance the portion from the free end (6) to the harvester head represents the portion of the stem from which the next log will be cut.

In a preferred embodiment a measurement is made of the time delay, $\Delta t$, between the production of the acoustic signal by the acoustic transmitting device (12) and sensing of the response from a single reverberation from the butt end (6) of the wood specimen (1) by the acoustic transmitter device. The distance, l, from the butt end (6) to the acoustic transmitter device is known from the movement of the tree through the harvester head. Therefore the longitudinal acoustic velocity can be calculated from equation (2). This velocity is then used to calculate the MOE according to equation (1).

An advantage of this transducer arrangement is that the acoustic signal is measured after travelling twice through the stem portion that is about to be cut. This increases the accuracy of any characteristic determined from the measurement by effectively doubling the size of the sample portion.

The acoustic signal produced by the acoustic transmitter device (12) will also travel in direction (16) to the other end (18) of the stem (1) and be reflected from the end (18) in direction (17) as shown in FIG. 6. In the embodiment shown in FIG. 6 the end (18) is the top of the stem (1).

The response of a single reverberation from the top end (18) may be sensed and used to determine the characteristic for the top portion of the stem in the same way as for the sample portion (ie butt end).

In a typical arrangement the harvester head will be closer to one end than the other of the stem. In most instances this will be the butt end.

A single transducer on the harvester head is used to produce the acoustic signal and to sense the response in the stem. In this arrangement the first signal sensed will be the single reverberation from the cut or butt end of the stem, as the distance travelled by the acoustic signal from the transducer to the butt end and back to the transducer is less than from the transducer to the top of the stem and back to the transducer. The next longitudinal signal sensed will be the first single reverberation from the top of the stem.

In the embodiment shown in FIG. 5 two acoustic transducers are provided to sense the acoustic signal in the stem. The transducer in the acoustic transmitter device (12) is adapted both to produce the acoustic signal and to sense the response in the stem (1). Transducer (13) is adapted to sense acoustic signals in the stem (1).

The arrangement of the acoustic transmitter device (12) and the receive transducers (12) and (13) allow the direction of the sensed acoustic signal to be determined as discussed above. The use of two transducers on the harvester head simplifies the signal processing by enabling the direction of the response to be determined.

FIG. 7 shows two acoustic signals (herein referred to as traversing acoustic signals), travelling in directions (19) and (20), that propagate substantially across the stem (1) from the acoustic transmitter device (12). Traversing acoustic signal (19) propagates from the acoustic transmitter device (12) towards the stem top end (18) with a plurality of internal reflections. Traversing acoustic signal (20) propagates from the acoustic transmitter device (12) towards the stem butt end (6) with a plurality of internal reflections.

Such acoustic signals travel with different properties from the acoustic signals travelling along the stem, for example, the traversing acoustic signals travel with lower velocity. Traversing acoustic signals decay comparatively rapidly.

Traversing acoustic signals may complicate the short duration measurement of the acoustic signals shown in FIGS. 5 and 6. As can be seen in FIG. 7 traversing acoustic signal (20) will be detected by transducers 12 and 13.

In the preferred embodiments the traversing acoustic signal is removed from the sensed response during signal processing if necessary.

In some embodiments the traversing acoustic signals is used to provide a measure of the radial acoustic velocity of the stem. The radial acoustic velocity are used to determine radial wood characteristics, using the same method as outlined above but substitution the radial measurements for the longitudinal measurements.

The radial characteristics, for example the radial strength, can be used to determine whether the wood is suitable for mechanical pulping, or should be chemically pulped.

The harvester head is designed to move the stem through the head rapidly and accurately. This enables a number of measurements to be made quickly at different positions along the stem in order to determine optimum cutting positions.

In a preferred embodiment the wood characteristic is determined prior to determination of the first timber length to be cut. The value of the characteristic is used, in combination with other data, for example wood diameter, sweep, and knot size, to determine the first cut timber length.

The information may also be used to grade and sort the cut logs at the time of cutting and stacking, leading to greater efficiency in the subsequent treatment of the logs.

Aspects of the present invention have been described by way of example only and it should be appreciated that modifications and additions may be made thereto without departing from the scope of the appended claims.

We claim:

1. A method for determining a characteristic of a portion of a wood specimen comprising the steps of:
    (a) producing an acoustic signal in the wood specimen part way along the length of the wood specimen wherein the distance from a first end of the wood specimen to the location where the acoustic signal is produced corresponds to a sample portion;
    (b) sensing a response in the wood specimen part way along the length of the wood specimen including a reverberation from the first end of the wood specimen; and
    (c) calculating a characteristic of the sample portion of the wood specimen from analysis of the sensed response.

2. The method of claim 1 wherein the acoustic signal is produced by a transducer acoustically coupled to the wood specimen.

3. The method of claim 2 wherein the transducer is a piezoceramic transducer stack.

4. The method of claim 2 wherein the transducer is configured to receive the sensed response.

5. The method of claim 1 wherein the acoustic signal is transmitted to the wood specimen by use of a spike.

6. The method of claim 1 wherein the acoustic signal is in the form of a frequency sweep.

7. The method of claim 1 wherein the acoustic signal is produced by an impact.

8. The method of claim 1 including the further step of sensing the response at more than one position on the wood sample specimen.

9. The method of claim 1 wherein the analysis requires sensing only a single reverberation from the first end of the wood specimen.

10. The method of claim 1 including the further step of measuring the time delay between the production of the acoustic signal and the sensed response.

11. The method of claim 10 wherein the time delay between production of the acoustic signal and sensing the response for a single reverberation from the first end of the wood specimen is used to calculate a characteristic of a portion of the wood specimen.

12. The method of claim 1 including the further step of using traversing acoustic signals to determine a characteristic of a portion of the wood specimen.

13. The method of claim 1, comprising the additional initial step of: moving the wood specimen through a harvester head until an end of the wood specimen extends a predetermined length from the harvester head; and wherein steps (b) and (c) are carried out proximate to or within the harvester head.

14. The method of claim 13 wherein the acoustic signal is produced and sensed by an acoustic transmitter device attached to the harvester head and coupled to the wood specimen.

15. The method of claim 13 wherein the method includes the further step of sensing a response at a second position in a portion of the wood specimen proximate to or within the harvester head.

16. A method of utilizing a characteristic of a portion of a wood specimen as determined by the method of claim 13 wherein the method includes the step of using the characteristic to determine the length of the log to be cut.

17. The method of claim 13, wherein the acoustic signal is produced by a transducer acoustically coupled to the wood specimen.

18. An apparatus for determining a characteristic of a portion of a wood specimen comprising:
    an acoustic signal generator;
    an acoustic transmitter device configured to provide an acoustic signal from the acoustic signal generator to the wood specimen part way along the length of the wood specimen wherein the distance from a first end of the wood specimen to the location where the acoustic signal is produced corresponds to a sample portion;
    at least one receiver configured to sense acoustic signals within the wood specimen including a reverberation from the first end of the wooden specimen;
    a processor electrically connected to the receiver; and
    wherein the processor is configured to determine a characteristic of the sample portion of the wood specimen from the sensed acoustic signals.

19. The apparatus of claim 18, wherein the acoustic transmitter device and the receiver are attached to a harvester head.

20. An apparatus for determining a characteristic of a portion of a wood specimen comprising: a harvester head; an acoustic signal generator; an acoustic transmitter device attached to the harvester head and adapted to provide an acoustic signal from the acoustic signal generator to the wood specimen; at least one receiver attached to the harvester head and configured to detect acoustic signals within the wood specimen including a reverberation from at least one end; a processor electrically connected to the receiver; and wherein the processor is configured to determine a characteristic of a portion of the wood specimen from the sensed acoustic signals.

* * * * *

UNITED STATES PATENT AND TRADEMARK OFFICE
CERTIFICATE OF CORRECTION

PATENT NO. : 7,603,904 B2  Page 1 of 1
APPLICATION NO. : 11/352466
DATED : October 20, 2009
INVENTOR(S) : Harris et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 301 days.

Signed and Sealed this

Fifth Day of October, 2010

David J. Kappos
*Director of the United States Patent and Trademark Office*